United States Patent [19]
Saunders

[11] Patent Number: 6,087,134
[45] Date of Patent: Jul. 11, 2000

[54] METHOD FOR ANALYZING DNA FROM A RARE CELL IN A CELL POPULATION

[75] Inventor: Alexander Michael Saunders, San Carlos, Calif.

[73] Assignee: Applied Imaging Corporation, Santa Clara, Calif.

[21] Appl. No.: 08/956,349

[22] Filed: Oct. 23, 1997

Related U.S. Application Data

[63] Continuation-in-part of application No. 08/783,522, Jan. 14, 1997.

[51] Int. Cl.[7] .............................. C12P 19/34; C12Q 1/68
[52] U.S. Cl. ................................ 435/91.2; 435/6
[58] Field of Search ................... 435/91.2, 91.1, 435/91.52; 428/18, 41, 42, 913; 156/157, 230, 236, 275.5, 307.1, 331.3, 331.6, 330, 331.8, 331.7

[56] References Cited

U.S. PATENT DOCUMENTS

| | | | |
|---|---|---|---|
| 3,715,293 | 2/1973 | Sander et al. | 204/159.14 |
| 3,801,329 | 4/1974 | Sander et al. | 96/115 P |
| 4,545,831 | 10/1985 | Ornstein | 156/57 |
| 4,624,915 | 11/1986 | Schindler et al. | 435/4 |
| 4,629,687 | 12/1986 | Schindler et al. | 435/4 |
| 5,432,054 | 7/1995 | Saunders et al. | 435/2 |

FOREIGN PATENT DOCUMENTS

| | | |
|---|---|---|
| 0 104 825 A1 | 12/1983 | European Pat. Off. . |
| WO 91/07660 | 5/1991 | WIPO . |
| WO 91/13838 | 3/1997 | WIPO . |

OTHER PUBLICATIONS

Marilyn J. Stapleton (1996) *Genetic Engineering News* p. 14 Sep. 1, 1996 Gene Amplification for Human Diagnostics.

Michael R. Emmert–Buck et al. (1996) *Science* 274:998 Laser Capture Microdissection.

C. G. Roffey (1982) *Photopolymerization of Surface Coatings* Chapter 4, John Wiley & Sons, New York Photopolymerizable Film–Forming Materials.

C. G. Roffey (1982) *Photopolymerization of Surface Coatings* Chapter 6, John Wiley & Sons, New York Photopolymerizable Film–Forming Materials.

*Pierce Catalog and Handbook* (1994–1995) pp. 0–92, T–155, T–156, T–157, T–163 T–164, T–165, T–169, T–170, T–174 and T–176.

Emmer–Buck et al. Laser capture microdissection. Science, vol. 274 (8), p. 998–1001, 1996.

Zekizawa et al. Prenatal diagnosis of Duchenne muscular dystrophy using a single fetal nucleated erythrocyte in maternal blood. Neurology vol. 46, pp. 1350–1353, 1996.

Vaigot et al, Cytometry 6(5): 422–7, 1985.

Heiden et al Virchos Arch B Cell Path 61(1): 29–38, 1991.

*Primary Examiner*—Eggerton A. Campbell
*Attorney, Agent, or Firm*—Townsend and Townsend and Crew LLP

[57] ABSTRACT

Methods are provided for analyzing DNA of a rare cell in a cell population. In one embodiment, the method involves covering a cell monolayer with a photosensitive material. By illuminating the area over a cell of interest, the material is solidified, permitting manipulation of the underlying cell and/or protection of the cell from DNA-inactivating agents that destroy DNA in other cells in the monolayer. In another embodiment, the monolayer is overlaid with a solid material that becomes soluble when illuminated. By illuminating the area over a cell of interest, that cell can be specifically exposed and DNA from the cell amplified. The methods are particularly useful for analyzing fetal cells found in maternal blood.

20 Claims, 4 Drawing Sheets

METHOD FOR ANALYZING DNA FROM A RARE CELL IN A CELL POPULATION

CROSS-REFERENCE TO RELATED APPLICATION

This application is a continuation-in-part of U.S. patent application Ser. No. 08/783,522, filed Jan. 14, 1997, the disclosure of which is incorporated herein by reference.

BACKGROUND OF THE INVENTION

Considerable advances have been made in recent years in screening for genetic traits, and DNA sequence data from the Human Genome Project, combined with advances in testing technology is expected to make genetic DNA-based testing increasingly common. See, e.g., Chee et al., 1996, *Science* 274:610–614. One area in which genetic testing is widely used is for prenatal screening of genetic traits. Most commonly, this analysis involves obtaining fetal cells by chorionic villus sampling (CVS) or amniocentesis, culturing the cells to metaphase, and generating a karyotype. However, both CVS and amniocentesis are invasive procedures which carry a risk of inducing miscarriage, and tend to be applied to mothers whose risk of bearing a chromosomally abnormal fetus exceeds that of the risk of procedure-induced miscarriage. In general, the procedures are offered to women over 35 years-old.

An alternative approach is analysis of fetal cells that cross the placenta and enter maternal circulation. Fetal blood cells are reported to enter the maternal circulation as early as 7 weeks post-conception and are found at a frequency of about 5 cells/ml of maternal blood from the first trimester onwards. Genetic analysis of these fetal cells could provide a safe and accurate way of screening for common aneuploidies (in particular Down syndrome) and other genetic traits. See, e.g., Chueh and Golbus, 1990, *Seminar Prenat.* 14:471; Zheng et al., 1993, *Med. Genet.* 30:1051–56; and Ganshirt-Ahlert et al., 1993, *Am. J. Reprod. Immunol.* 30:194–201. Thus, a need exists for new methods for isolating and analyzing DNA from fetal cells in maternal circulation.

There is also a need for new methods of isolating DNA from cells, other than fetal cells, that are present at low frequency in a population of cells. For example, methods for isolation and analysis of rare malignant cells present in a population consisting primarily of non-malignant cells would aid in diagnosis and treatment of disease (e.g., screening for a genetic lesion giving rise to the malignant state). Thus, a need also exists for improved methods for DNA analysis of various types of rare cells in a population.

SUMMARY OF THE INVENTION

In one aspect the invention is a method for analyzing DNA of a rare cell in a cell population, for example fetal cells found in maternal blood. According to the method, cells are applied to a surface, the rare cell(s) of interest are located and overlaid with a cover layer of a material that becomes solid when illuminated by light of a certain wavelength (a solidifiable material). The cover layer is illuminated with light focused at the location of the rare cell, causing a solid plug to be formed at that location. In some embodiments, the solid plug lies over a single cell or a single cell type. In one embodiment, the solid plug is removed and a cell adhering to the plug is used as a source of DNA or RNA for analysis. In a second aspect, prior to removal of the solid plug, the unsolidified material is washed from the surface, exposing the underlying cells. DNA in those cells, but not in the cells protected by the a solid plug, is inactivated by exposure to a DNA-inactivating agent such as DNAse I. Following destruction of the DNA in unprotected cells, the DNA inactivating agent is removed. The plastic plug is then removed, and the DNA from the underlying cell (i.e., the rare cell of interest) is analyzed.

In another aspect, the invention provides a method for selectively amplifying DNA of a rare cell in a cell population using positive photoresist technology. According to this method, cells are applied to a surface which is overlaid with a photodepolymerizable coating (i.e., one that become soluble after irradiation at certain wavelengths) and treated (e.g. using heat) to form a solid. The cover layer is illuminated at the location of the rare cell, to increase the solubility of the material at the location (i.e., depolymerize the material), the soluble material is removed. The result is that a "well" is formed in which the rare cell sits. Reagents (e.g., PCR reagents) can be added to the well and DNA from the rare cell analyzed (e.g., by amplification).

DETAILED DESCRIPTION OF THE INVENTION

Figure 1:
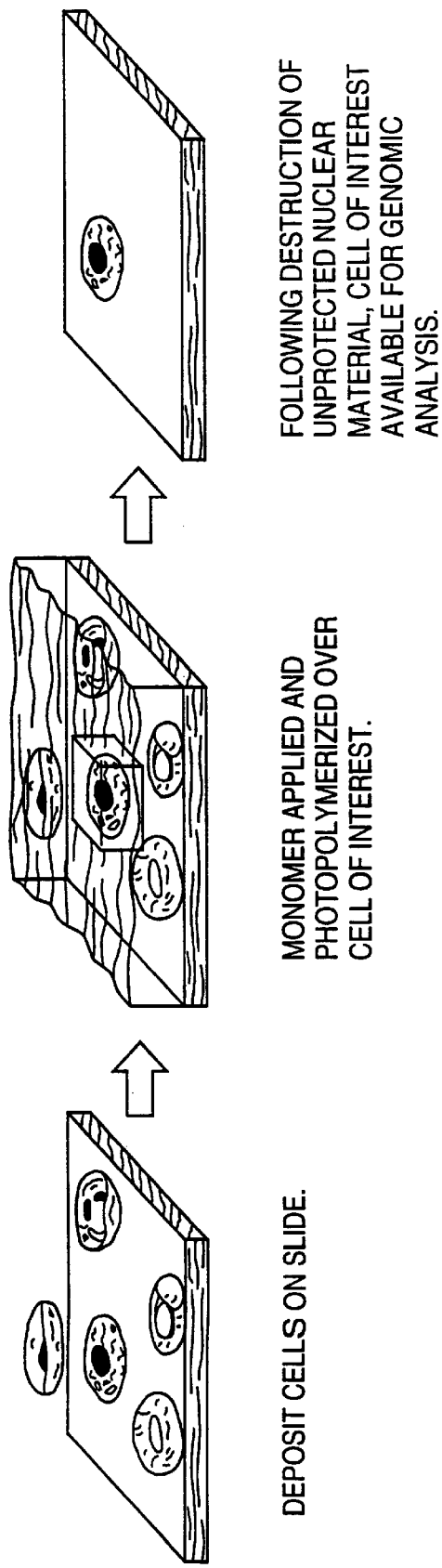
FIG. 1 is a schematic showing the strategy used for protecting the DNA of a rare cell of interest on a microscope slide.

In one aspect, the invention is a method for analyzing DNA from a rare cell in a cell population. A cell population that includes a cell of interest is applied as a monolayer to a surface, such as a slide, and the location of the cell or cells of interest is determined. In one embodiment, a liquid composition or suspension is then applied over the monolayer of cells. The liquid composition, typically including components of a plastic, is photosensitive and forms a solid (e.g., by polymerization or cross-linking of the plastic components) upon illumination. Thus, by focusing light over the cell of interest, it is possible to cause a solid plug to form over a small defined area, such as over only a single cell or small number of cells. When the non-solid material that remains over most of the cells in the monolayer is removed, usually by washing the slide in a solvent, the solid plug is left in place over the cell of interest. In one embodiment, (i) the cover layer over the cell of interest is illuminated and becomes solid, (ii) optionally the unsolidified material is washed away, and (iii) the solid plug is removed from the slide with the underlying cell of interest remaining adherent to the plug. The cell of interest, thus isolated from other cells in the population, is then subjected to analysis, typically by amplification of its DNA. In a second embodiment, following the removal of the non-solid material, a DNA-inactivating agent (for example, an enzyme) is applied to the surface. The DNA-inactivating agent destroys the DNA in unprotected cells, but does not have access to the cell or cells of interest, i.e., those underlying the solid plug(s). After treatment with the DNA-inactivating agent, the solid plug is removed. When the cell of interest adheres to the slide it may be subjected to analysis in situ or after transfer to another vessel. Similarly, when the cell adheres to the solid plug, it may be analyzed, usually by amplification of DNA. A cell is said to "adhere" to the plug when it remains associated with the plug when the plug is removed from the surface.

In a second aspect, the DNA from a rare cell in a population is isolated using positive photoresist technology. This method is carried out by covering a monolayer of cells with a material that can be made solid, typically be exposure to heat, but which can be solubilized locally by irradiation with light. The covering material is solubilized over the rare cell(s) by illuminating the cover material in that location. When the solubilized material is removed, the result is a "well" in which the rare cell is contained, but exposed. Amplification of the DNA in the cell of interest is carried out by adding reagents (e.g., PCR reagents) to the "well."

The invention will now be described in some detail.

A) Source of Cells

Although in theory the present method can be used to isolate any cell in a population, it will be most useful when analysis of a rare cell type is desired. Thus, the cell population will be a mixture of cells of interest and other cells. A cell type is considered a "rare cell type" when it represents less than about 10% of the cells in a biological sample. Usually, however, the rare cell will represent much fewer than 10% of the cells in a population. Typically the rare cell will represent fewer than about 1% of the cells in a population, often fewer than about 0.1%, frequently less than about 0.01%, and very often, as in the case of fetal cells in maternal circulation, fewer than about 0.0001% of the cell population from which it is derived (e.g., the population of cells in maternal whole blood). In one embodiment of the invention the rare cell type is a fetal cell obtained from maternal blood, especially a nucleated fetal cell such as a nucleated fetal red blood cell (nfRBC). In another embodiment, the rare cell is a fetal reticulocyte in a population of maternal cells.

Cell populations containing rare cells of interest may be from a variety of biological sources including whole blood or blood fractions, saliva, bronchoaveolar lavage and tissue biopsies. In a preferred embodiment the genetic composition of a fetus is of interest and maternal blood is used as a source of cells. Maternal blood may be obtained by standard methods. It will often be desirable to enrich the maternal blood sample for fetal cells. Preferred methods for enrichment are described in U.S. Pat. No. 5,432,054 and International Patent application WO 91/07660, each of which is incorporated herein by reference.

In another embodiment, the rare cell type is a malignant (i.e., cancer) cell. A cancer cell of interest may be obtained by biopsy, from blood, or from a tissue section, or from a touch preparation of fresh tissue onto a slide.

B) Preparation of the Monolayer

According to the invention, the population of cells including the rare cells of interest is applied in a monolayer on a support such that the cells can be viewed using a microscope. Generally the support will be a glass or plastic slide, a chamber slide, a tissue culture plate, or a plastic film. A preferred support is a glass slide imprinted with a label(s) that allow accurate positioning or repositioning (i.e., within +/−10 microns) on a microscope stage.

When glass or plastic slides are used, they will usually be washed (e.g., with ethanol) before use and will often be pre-treated to affect the adherence of the cells or tissue section. Methods for pretreatment of slides include coating with materials such as poly-L-lysine, agarose, alginate, cellulose or chondroitin sulfate. A potential advantage to pre-coating the slide is that, upon removal of the solid plug formed according to the method of the invention, the underlying cell of interest can be caused to either remain on the coated slide or, alternatively, be removed along with the solid plug. For example, treating a glass slide with poly-L-lysine will tend to make a cell adhere to the slide rather than an overlying plastic plug. In contrast, when a slide is covered with cellophane the cell will tend to adhere to the plastic plug.

A monolayer is defined as being a layer of cells that is, on average, less than one cell deep. When a source of cells other than a tissue section (e.g., a cell suspension) is used, it is desirable to control the cell density so that, on average, there is at least about 1–3 cell diameters between cells. A typical sample of maternal blood enriched for fetal cells as described in U.S. Pat. No. 5,432,054 will yield approximately 15 target nfRBCs per 2 microliter sample, with a background of approximately 200,000 total nucleated cells. Thus, a useful balance between cell density and an high number of target cells per slide can be achieved by applying 2 μl of such a sample to a 25 mm×75 mm glass slide, so as to cover about 160 mm$^2$ of the slide.

Monolayers of blood are easily produced by well known methods including preparation of wedge smears. When the sample containing the cell population is fluid (e.g., blood or a cell fraction such as blood enriched for nucleated fetal cells) the technique of "centrifugal cytology" is useful for the preparation of monolayer slides with controlled cell density and adequate morphology. According to this method, a dilute suspension of cells is placed in an assembly in which a microscope slide forms the bottom of a sealed cylinder. The assembly is centrifuged to drive the suspended cells onto the slide. After centrifugation, the cells remain on the slide and may be processed like a routine blood film.

Although a cell suspension (e.g., blood) is a preferred source of cells for the monolayer, a tissue section (e.g., a section prepared using a microtome) can also be used. When tissue sections are used, there may be optional pretreatment by freezing, fixation by conventional fixing agents and/or embedding (e.g., in paraffin). When a tissue section is used (e.g., a section from a malignant tumor) it will be apparent that the plug should be formed over either one or more malignant cells (but no normal cells) or one or more normal cells (but no malignant cells), so that they can be separated from each other.

Fixation of cells from a suspension or tissue section will generally facilitate their handling. When fixed cells or tissue is used, it will be appreciated that the method of fixation should be chosen so as to retain nucleic acids (e.g., DNA and/or RNA) in a form capable of amplification. Methods for tissue fixation which are compatible with subsequent amplification or other analysis of nucleic acids are well known and include treatment with 80% ethanol, 100% methanol, 100% acetone, and mixtures of these reagents. In some embodiments fixation is carried out at low temperature (e.g., −20° C.).

C) Detecting the Rare Cell of Interest

A rare cell of interest can be detected or identified on the basis of its morphological, biochemical, genetic, or other characteristics. Histochemical staining is especially useful for identification of a rare cell of interest. Immunological labeling is another method that can be used to identify a cell of interest. According to this technique, an antibody specific for an antigen whose presence (or absence) is characteristic of a rare cell of interest is bound to the cell and directly or indirectly labeled. Immunolabeling techniques are well known and are described generally in Harlow and Lane, *Antibodies: A Laboratory Manual*, Cold Spring Harbor, N.Y. (1988), which is incorporated herein by reference.

When the rare cell of interest is a nucleated fetal red blood cell, the cell can be identified based on the density of staining, the shape and size of the nucleus and cytoplasm, or other by immunohistochemical methods (e.g., anti-$Hb_\gamma$ or anti-$Hb_e$). One useful method for identifying nfRBCs entails subjecting the cells in the sample to a Kleihouer-Betke extraction (Betke, 1968, *Bibliotheca Hematologica* 29:1085–93), followed by staining of nuclei with Astrazon Blue. The Kleihouer-Betke extraction destroys adult hemoglobin so that only fetal hemoglobin, if it is present, remains. Astrazon Blue staining may be carried out using 0.005% Astrazon Blue, pH 5.5, for 3 minutes followed by three immersion rinses in deionized water. If cells extracted and stained in this manner are viewed using a microscope fitted with a blue filter (i.e., which transmits light of the wavelength absorbed by the hemoglobin, e.g., 415 nm +/–5 nm), nfRBCs appear to have light nuclei and dark cytoplasm. In contrast, maternal cells appear transparent and can be readily distinguished from nfRBCs.

However detected, the location of the cell of interest on the support (e.g., slide) is determined and recorded. In one embodiment, the cell is located visually on the slide and the position of the cell (i.e., stage coordinates) is noted. In a preferred embodiment, an automated microscope is used. In this embodiment, the microscope is equipped with a motorized stage, a computer based image analysis system (including algorithms for automated focusing and cell detection), and a means for storing the location (i.e., coordinates on the slide) of an identified rare cell, so that cells of interest can be precisely relocated. An example of an automated microscopes that includes a motorized stages is the LSC microscope (CompuCyte Corp., Cambridge Mass.). The image analysis software typically includes a means for distinguishing a cell of interest from other cells in the population (e.g., by evaluation of the shape and size of the nucleus and cytoplasm, differential evaluation of images taken using different filters that reveal differences in cell staining) and for recording the location of the cell in the slide.

D) Differential Protection of DNA from Rare Cells of Interest

In a preferred embodiment of the invention, DNA from a rare cell of interest is sequestered from that of other cells in the population. Thus, in the case of a nucleated fetal red blood cell, the cell is sequestered from nucleated (DNA-containing) maternal cells. This is carried out by covering the cell monolayer with a composition that, when illuminated in a defined area, forms a solid in that area (e.g., at the location of the rare cell on the surface but not over other cells on the surface). As used herein, a composition that solidifies upon illumination is referred to as a "solidifiable" composition or material and a composition that does not form a solid upon illumination, even though it may solidify under other conditions (e.g., exposure to heat), is specifically excluded. In one embodiment, the solid material formed by illumination protects DNA in the underlying cell(s) from destruction or inactivation by a DNA-inactivating agent. It will be appreciated that a large number of solidifiable composition are suitable for use in the invention. Typically, the solidifiable composition includes organic subunits (e.g., plastic monomers) plus a photoinitiator or a light-activated (i.e., photoreactive) cross-linking agent, so that, upon illumination, the subunits polymerize or cross-link to form a solid network.

Two broad classes of solidifiable compositions are compositions that become solid through a process of photopolymerization, and compositions that become solid by cross-linking. However, the distinction between polymerization and cross-linking is not necessarily precise and formation of some solids may involve both processes. It will be appreciated that the mechanism by which the material is solidified is not critical, so long as the underlying cell is protected from the DNA-inactivating treatment.

Typically, polymerization is characterized by the joining of simple monomers to each other, or to pre-existing oligomers or polymers, to form a high molecular weight molecule, i.e., a polymer. The polymer may be linear or branched, and may be made from identical monomers, or from two or more different monomers (whereupon a "copolymer" is formed). The speed of polymerization in the solidifiable compositions used for practice of the invention is controlled by a photoinitiator, typically an agent that forms free radicals when illuminated by light of appropriate wavelengths.

In contrast, cross-linking occurs between light-sensitive polymers (polymers possessing in their chain a photosensitive functional groups, or between polymers in the presence of a photoreactive cross-linker. Examples of photoreactive cross-linkers include BASED (Bis-[β-(4-azidosalicylamido) ethyl] disulfide), ASBA (4-(p-Azidosalicylamido) butylamine), and ASIB (1-(p-Azidosalicylamido)-4-(iodoacetamido)butane). These cross-linkers, as well as others, are available from the Pierce Chemical Co., (Rockford, Ill.) and are described in the Pierce Catalog and Handbook 1994-1995 Edition,which is incorporated herein in its entirety and for all purposes. BASED has useful properties based on a central disulfide bond between two aryl azido groups. Once the azido groups are photoactivated to link to amino groups in a substrate, the substrate is effectively cross linked. However, the disulfide links may be broken by exposure to a sulfhydryl compound such as dithiothreitol. Thus, when BASED, or similar materials, are used, the protective layer over a cell of interest may be removed easily by exposure to a sulfhydryl compound.

Monomers useful in polymerization reactions include ethylene, styrene and substituted stryenes, propylene, vinyl, vinyl alcohols, vinyl acetals, methacrylate, urethane, neopentyl glycol dimethracrylate, poly bis phenol A-co-epichlorohydrin, epoxy resins (e.g., 5 minute epoxy) and bis-phenol A type epoxy acrylate oligomer, polyethylene glycol dimethacrylate, penta-erythritol tetracrylate, urethane acrylate oligomer, neopentyl glycol dimethracrylate, polyethylene glycol dimethracrylate, methylphenylglyoxylate, polybutylmethacrylate, and trimethylol trimethacrylate. Small proportions of bifunctional monomers (e.g., divinylbenzene) may be added to form cross-links during polymerization.

A broad spectrum of photoinitiators can be used in the invention. Typically, free-radical generating photoinitiators will be preferred. Preferred photoinitiators include 2,2-dimethoxy,2-phenylacetophenone and 2,2-diethoxyacetophenone. Other photoinitiators are listed and described in U.S. Pat. Nos. 3,715,293 and 3,801,329, both of which are incorporated herein in their entirety and for all purposes.

Materials capable of photopolymerization and photo-induced cross-linking are described in C. G. Roffey *Photopolymerization of Surface Coatings* John Wiley & Sons 1982 which is incorporated herein by reference, in its entirety and for all purposes.

It will be appreciated that the solidifiable material will have certain characteristics: (i) It should be capable of being locally solidified, i.e., cross linked or polymerized in a defined area, (ii) the resulting solid material (e.g., plastic plug) should protect underlying cells from exposure to a DNA-destroying agent such as DNAse; and, (iii) where not exposed to illumination, the material should be removable from the support on which the monolayer sits. In addition, it is desirable that the material be easily applied, that it be transparent (prior to solidification) to allow viewing of underlying cells, and that, upon activation of the photoinitiator or photocross-linking agent, a solid is formed within about 5 minutes, more usually in less than about 2 minutes. Once solid, the solidifiable material should provide a barrier to a DNA-inactivating treatment such as a bovine pancreatic DNAse I (11.5 units/ml in PBS containing 6% BSA and 10 mM magnesium acetate) for 30 min. at 37° C. such that the DNA of an underlying cell is not inactivated by the treatment.

The solidifiable material may be formulated in a variety of ways. For example, the proportion of photoinitiator or photocross-linking agent in a solidifiable mixture will typically be one part in ten (i.e., about 1 part photoinitiator to 9 parts mixture of monomers and polymers), but may vary considerably (e.g., from about 1% to about 25%). In addition, the viscosity of the material may be adjusted. In general, the solidifiable material should have a viscosity such that a thin film (e.g., from about 5 $\mu$m to about 1 mm, more usually from about 10 $\mu$m to about 200 $\mu$m) forms over a slide that is dipped into the liquid mixture. To achieve this viscosity, it will sometimes be useful to mix solid polymer in with the uncrosslinked components. Examples of solid polymers that may be added to the uncross-linked mixture include polyester resin, poly bis phenol-A-coepichlorohydrin (glycidyl end-capped), and polystyrene. The amount of solid polymer to be added will vary, but typically will be between 1% and about 25% (w/w), more usually between about 10% and about 20%.

Although it will generally be the case that the substrate (monomer(s) and/or polymer(s)) and the photoinitiator or cross-linker will be mixed together before being applied to the slide, it may sometimes be the case that they will be applied sequentially to the slide or other support.

One of skill will be able, using routine testing, to determine whether a particular composition has the properties desired. One test for suitability of a material is carried out as follows. Five slides are prepared by applying a blood monolayer, fixing the cells using 80% EtOH, and staining with a DNA stain (e.g., Astrazon Blue). The solidifiable material is applied to each of the slides, overlying the monolayer. On each slide, one or more non-overlapping regions (containing cells) are identified and these areas are exposed to radiation of an intensity and wavelength known to activate the photoinitiator or photoreactive cross-linking agent, or, if the activation properties of the photoinitiator or crosslinker are not known, with high intensity broad band irradiation (e.g., a 100 W mercury arc lamp focused on the slide by the microscope condenser), without illuminating other areas of the slide. The duration of illumination differs for each slide, e.g., 10 sec., 30 sec., 1 min., 2 min. and 5 min. Following illumination, the nonsolidified material is removed, and the whole slide is treated with dilute acid (e.g., 0.01 N HCl for 1 hour at 60° C.) to destroy DNA in unprotected cells. The slide is examined using a microscope. When a suitable composition is used, at least one slide will have stained cells (i.e., having intact DNA) in the illuminated areas and no (or very few) stained cells in the non-illuminated areas. If desired, further testing may be carried out in which DNA from the stained cell is amplified using the polymerase chain reaction using primers chosen to amplify a 0.2–1 kb fragment from the cell type of the stained cell.

In some embodiments, a tracer (e.g., dye) is added to the solidifiable material so that solid plugs can be more easily visualized (or otherwise detected) before, during and after removal of the plug or transfer of the plug and underlying cell to a tube. In one embodiment, the tracer is a fluorescent dye. It is desirable that the added tracer be soluble in the solidifiable material (e.g., monomer) and solvent used to remove the unsolidified monomer. For example, when a toluene-soluble monomer mixture is used, 2,5-bis-[5-tert-butylbenzoxazolyl]-thiophene (BBOT) or 1,4-[bis-(5-phenyloxazolyl)]-benzene (POPOP) are suitable because they are soluble in toluene. Both these compounds emit bright blue fluorescence when illuminated by UV light (e.g., at 360 nm). Typically, the fluorescent compound is dissolved directly in a small aliquot of pre-formulated monomer together with the photoinitiator to form a stock solution and added to (diluted in) the monomer to make "fluorescing monomer" as required. The monomer is applied to the slide (e.g. forming a layer approximately 100 microns thick), the area over a cell of interest is illuminated, and unsolidified (e.g., unpolymerized) material is removed (e.g., by a toluene wash), all as described herein. If the slide is then placed near a UV light source (e.g., a UV light box), the microscopic plug is clearly visible, and may be easily manipulated (e.g., with fine tipped forceps). In cases in which a fluorescent dye that has an excitation wavelength that overlaps the wavelength required for photoinitiation is used as a tracer, the illumination time required for polymerization may be slightly increased (e.g., from about 15 seconds to about 30 seconds).

The cell monolayer may be overlaid with the solidifiable material in a variety of ways. In one method, a drop (e.g., about 50–200 $\mu$l) of the mixture is applied over the monolayer on a slide. Application of a cover glass two-thirds as long as the slide (24×60 mm) is used to facilitate the formation of a thin film by capillary action. The coverglass is then removed by smoothly sliding it horizontally across the slide, leaving a thin film of material over the monolayer. Alternatively, the solidifiable material may be applied by dipping, spraying, or other means. The solidifiable material may be applied either before or after the cell(s) of interest is located.

Although the solidifiable material and solid plug are described as lying "over" the cell of interest, it will be appreciated that in many cases, a more precise description would be that the material overlays and surrounds the cell of interest. This is because usually there will be space between cells in the monolayer.

E) Illumination Source

According to the present invention, a solid is formed over the rare cell of interest after focused illumination when a cover layer of a solidifiable material is illuminated at the location of a rare cell on the surface. As used herein, the terms "illumination" and "irradiation" are used interchangeably. It will be understood that the "location" of the rare cell refers to the area including the rare cell but not including other cells in the population or one the surface. Suitable sources of illumination are any source that emits radiation from about 360 nm to about 700 nm. The preferred wavelength of the illumination will depend on the particular photoinitiator or cross-linking agent used. Most often, a source that emits non-ionizing radiation from about 400 nm to about 570 nm.

Suitable illuminating sources include mercury arcs, carbon arcs, tungsten filament lamps, xenon arcs, krypton arcs, sunlamps, lasers, and the like, with mercury arcs, e.g., a 100 W mercury arc lamp, most preferred. Often, multichromatic light will result in most efficient photopolymerization. The use of multichromatic light for photopolymerization is described in U.S. Pat. No. 3,715,293, which is incorporated herein by reference. However, monochromatic light, e.g., laser light, is also useful and has certain advantages. For example, the small beam diameter of many lasers can be used to illuminate a small diameter area, e.g., an area over a chromosome. In some cases it will be desirable to place an infrared filter between the light source and the target to avoid the generation of large amounts of heat.

In a preferred embodiment, the source and intensity of illumination will be chosen or adjusted so that the solidifiable material polymerizes or cross-links within about 2 minutes exposure time. The amount of time required for solidification (e.g., polymerization) will depend on a number of factors including the type of lamp used, the wavelengths emitted (or when light filters are used, the wavelengths of the radiation striking the solidifiable material), the thickness of the layer of solidifiable material, and the efficiency of demagnifying the image of the light source onto the slide.

Figure 2:
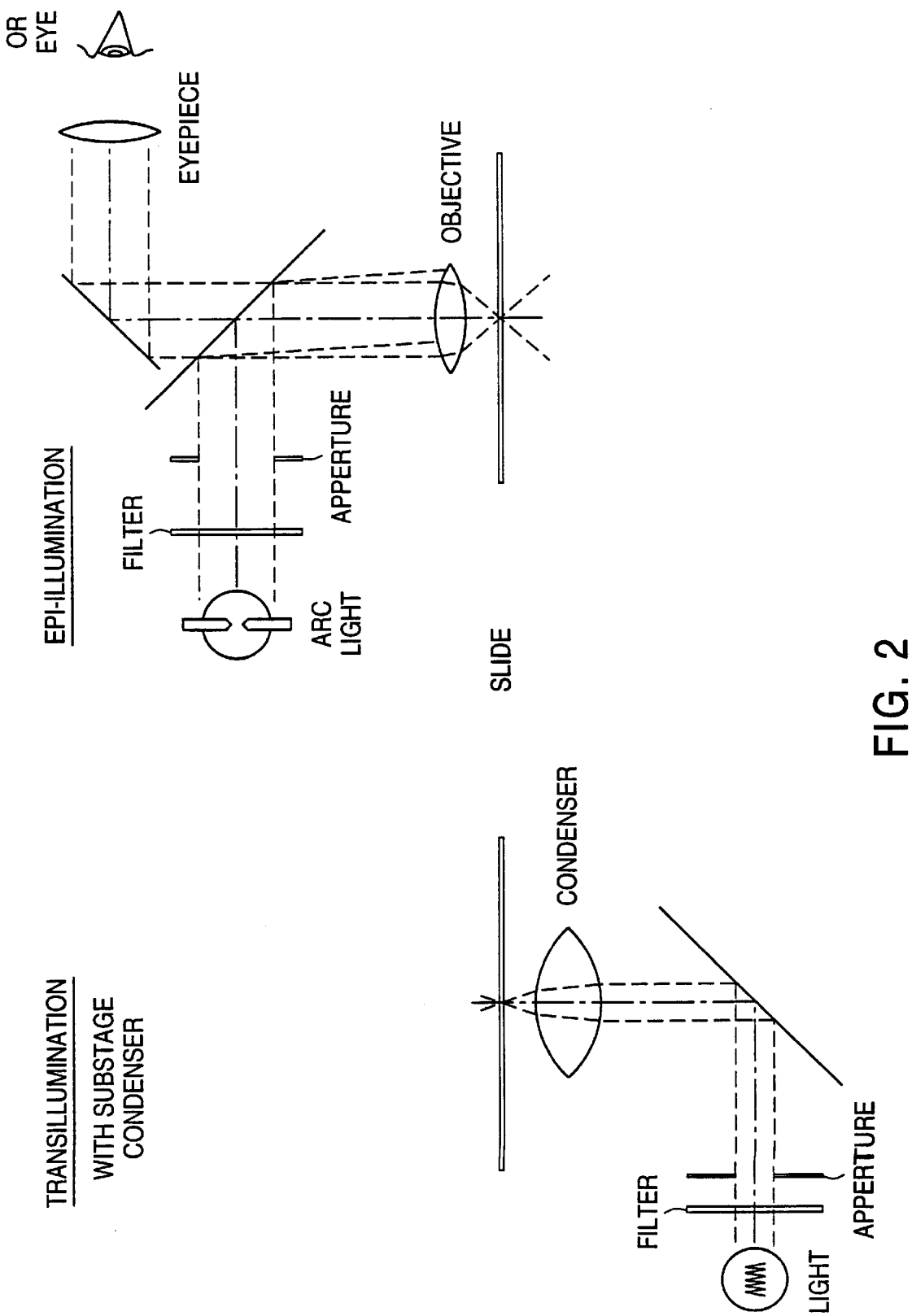
FIG. 2 is a diagram showing the relationship of an aperture, slide, and light source in microscopes using transillumination or epi-illumination.

The size of the solid (e.g., photopolymerized plastic) plug can be controlled by varying the size of the aperture placed in the light path between a lamp and the slide, and by the magnification of lenses between the light source and slide. FIG. 2 is a diagram showing the relationship of an aperture, slide, and light source in microscopes using transillumination or epi-illumination. The size of the plug can also be affected to some extent by varying the illumination time. Using these techniques, solid plugs of a range of diameters can be made by using various apertures. For example, a 10-micron diameter plug may be made (compared to a single RBC diameter of about 7 microns), although it is usually not necessary to make plugs this small for isolation of a specific cell(s) of interest. More usually, the plug will be in the range of about 15 to about 200 microns in diameter.

F) Removal of Uncrosslinked or Unpolymerized Material

In some embodiments, following illumination over the cell(s) of interest, unpolymerized material is removed, leaving a solid "plug" which protects the target cell. The method of removal will depend on the precise characteristics of the material. Usually the slides are dipped in an organic solvent to remove unpolymerized or uncross-linked material, and allowed to air dry. A variety of organic liquids will be suitable, with toluene, or toluene followed by 2,2-dioxane most often preferred. The total time in organic solvent is chosen to completely remove the unpolymerized monomer and may be as short as about 0.25 minutes or as long as about 10 minutes or longer; typically the treatment with organic solvent is between about 2 and about 4 minutes. It will be apparent that the solvent for unpolymerized material should not also be an efficient solvent for the solid material. For example, polystyrene is soluble in toluene, so when the styrene monomer is used alone, unpolymerized material should be removed using a solvent such as light petroleum ether or other mixture of solvents or mixtures that can be easily determined by experiment.

Uncrosslinked polymers are also soluble in their own monomers and in similar solvents. Polystyrene, for example, is soluble in monomeric styrene as well as in toluene and other solvents. Thus, if the solid material is a cross-linked polymer, uncross-linked material can be removed by exposure to a solution of monomer.

G) Inactivating DNA in Unprotected Cells

In some embodiments, after the rare cells of interest are protected by a layer of solid material, the slide is exposed to an agent or agents which inactivate (e.g., hydrolyse) DNA in cells not covered by a solid plug. As used herein, DNA is "inactivated" when DNA from the treated cells cannot be amplified by the polymerase chain reaction using primers and conditions that result in an expected amplification product in untreated cells of the same type. In human cells, a useful assay is for X or Y-chromosome specific markers (see, e.g., Decorte et al., 1994, Am. J. Hum. Gen. 54:506–15, and Lo et al., 1993, Human Genetics 90:483–88, both of which are incorporated by reference in their entirety for all purposes.) A second useful assay is fluorescent in situ hybridization using a X- and/or Y- chromosome specific probes, in which hybridization does not occur after treatment, but does occur in untreated cells of the same type. Examples of DNA-destroying treatment include exposure to DNAse, and hydrolysis at low pH. However, it will be recognized that other methods for destroying DNA are known.

1) DNAse

In one embodiment, slides containing one or more cells of interest protected by the solid plugs are treated with bovine DNAse to hydrolyse DNA. DNAse is readily available from suppliers (e.g., Sigma Chemical Co.). Usually treatment is for between about 5 minutes and about 60 minutes, typically about 30 minutes using a DNAse concentration of between about 5 and about 30 Kunitz units of DNAse per ml of buffer (e.g., PBS) in the presence of magnesium (e.g., 10 mM), typically between about 10 and about 15 units per ml. One Kunitz unit will produce a $\Delta A_{260}$ of 0.001 per min per ml at pH 5.0 at 25° C. using DNA, Type I or III as a substrate. See Linberg, 1967, Biochemistry 6:335. Following DNAse treatment slide excess DNA is usually removed by immersing the slide several times in PBS.

2) Hydrolysis at Low pH

DNA may be inactivated by exposure to low pH, for example using the Feulgen reaction. The Feulgen reaction (see Feulgen and Rossenbeck 1924 J. Phys. Chem. 135: 203; Pearse and Everson, 1960, Histochemistry, 2nd Edition, J. & A. Churchill, Ltd.) is a method of treating blood films or paraffin sections with 1 N HCl at 60° C. , e.g. for 60 min to cleave nucleotides in the sample. Ethidium bromide may be used to detect any DNA remaining after treatment with HCl.

H) Removal of Solidified Material

Figure 3:
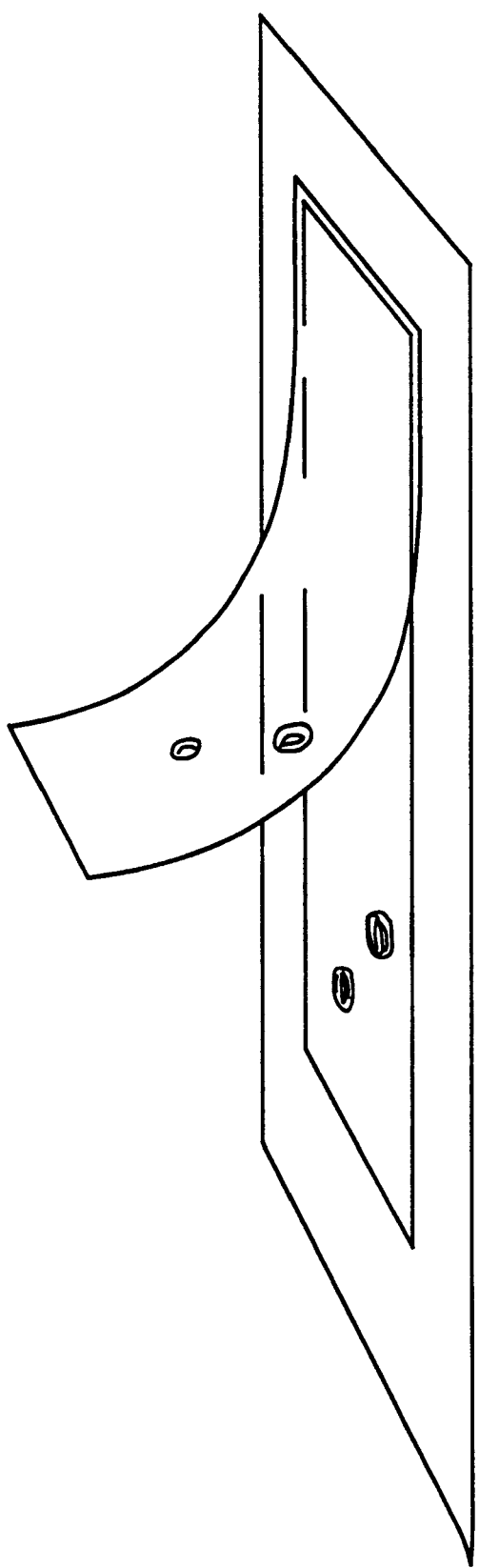
FIG. 3 is a diagram showing the use of an adhesive tape to lift a solid plug from a slide.

The solid plug(s) may be removed manually (e.g., using forceps, or an adhesive material to grip the upper surface of the plug) or using automated equipment. In one embodiment, the target cell or cells are exposed by carefully applying a firm pressure to the edge of the plastic plug until it is released from the slide. Manual removal is limited to plugs that are large enough to manipulate with forceps, i.e., roughly equivalent to at least about 10 cell diameters. FIG. 3 is a diagram showing the use of an adhesive tapeto lift a solid plug from a slide.

Upon removal of the solid plug from an untreated surface, the cell may remain attached to the surface, or may be removed along with the plug. It is possible to tell by visual (i.e., microscopic) examination or other means whether or not the rare cell of interest has adhered to the plug or the slide, particularly when the cell has been stained. When the cell of interest remains attached to the solid plug, the plug can be carefully transferred to a sterile tube for amplification of the genetic material, if it is present, e.g., using the polymerase chain reaction (PCR). It is not necessary to determine in advance whether or not the cell has remained attached to the solid plug in any particular instance. Instead, the location of the cell can be determined from the results of analysis. For example, when analysis is by PCR, a positive control may be included so that, in addition to analysing a particular chromosomal locus, a control sequence present in all rare cells of interest is also amplified.

If the target cell remains on the slide, the cell can be analyzed using fluorescence in situ hybridization (FISH) or, alternatively, amplification can be carried out by constructing or placing a plastic ring around the cell on the slide. PCR reagents (e.g., buffer, polymerase, and dNTPs) are added to the well, overlaid with oil or other means to prevent evaporation, and the PCR reactions carried out (i.e., using a thermocycler or series of hot plates).

I) Analysis of Cellular Nucleic Acids

PCR and its variants are well known and are described generally Innis et. al. (eds.) *PCR Protocols: A Guide to Methods and Applications*, Academic Press Inc. San Diego, Calif. (1990), and in U.S. Pat. Nos. 4,683,195 and 4,683,202, all of which are incorporated herein by reference. As is well known, to amplify DNA from a cell, it is not necessary to purify or isolate the DNA from the other cellular components. Instead, an intact or partly disrupted cell can be added to an amplification mixture and PCR carried out. Analysis and amplification methods other than PCR, for example, the ligase chain reaction, can also be applied to the DNA from a cell isolated according to the method of the invention (see, e.g., P. Tijessen, 1993, *Hybridization With Nucleic Acid Probes* Elsevier Science Publishers B.V., chapter 5, which is incorporated herein by reference). It will be understood by those of skill that "amplification of DNA" in a cell refers to amplification of a fragment of cellular DNA. Amplification of cellular RNA can be carried out using reverse-transcription-PCR (RT-PCR), which is well known in the art (see, e.g., Innis et al., supra, and Ausubel et al., Current Protocols in Molecular Biology, Greene Publishing and Wiley-Interscience, New York (1997)). Amplification of RNA may be used in combination with, or as an alternative to, amplification of DNA. In one embodiment, RNA (cDNA) is amplified from fetal reticulocytes in maternal blood and the product analyzed. In another embodiment of the invention, the expression of a mRNA in a malignant cell is determined after the malignant cell (or several malignant cells in the same field) are separated from non-malignant cells.

J) Isolation of Chromosomes

In an alternative embodiment, the solidifiable material is used to isolate a single chromosome from a cell. In this embodiment, chromosomes are applied to the surface. Typically this is done as a metaphase spread using well-known techniques (see, e.g., Ferguson-Smith and Andrews "Cytogenetic Analysis" in Rimoin et al., 1997, *Medical Genetics* 3rd Ed. Churchill Livingstone, New York). The solidifiable material is applied over the chromosomes and a chromosome of interest is identified. Preferably, the chromosome of interest is well separated from other chromosomes on the surface. Using a source of illumination, usually a laser, the solidifiable material is polymerized over the chromosome, forming a plastic plug. The chromosome of interest can then be isolated in the same manner as is described above for cells.

K) Positive Photoresist

An alternative embodiment of the invention, referred to herein as "positive photoresist," allows analysis of the DNA of a rare cell using a method similar in principle to those described above. In this method, the cell monolayer is coated with a material that can be made solid (e.g, by treatment with heat, with heating at less than 100° C. preferred, with less than 90° C. most preferred) but which is rendered soluble upon exposure to light of an appropriate wavelength (i.e. actinic radiation) and treatment with a suitable developer. Light is focused over the cell(s) of interest to render the material overlaying and surrounding the cell of interest soluble in a developing solution. The solubilized material is removed (e.g., by rinsing the slide with a solvent) with the result that the cell of interest sits on the slide at the bottom of a "well" whose walls are solid. The DNA of the rare cell is thus accessible to analysis. When analysis is by PCR, one method is to add amplification reagents (e.g., buffer, enzyme and dNTPs) to the "well," overlay the reaction mixture with oil to impede evaporation, and expose the slide to thermocycling using a commercial thermocycler or the equivalent, or a series of hot plates for heating and cooling the slide.

Materials and methods useful in this technique are well know, and heretofore have been used primarily in the microelectronic arts. Descriptions of such materials found in C. G. Roffey *Photopolymerization of Surface Coatings* John Wiley & Sons 1982, Chapter 6 ("Photoresist Technology"), in Moreau *Semiconductoir Lithography: Principles, Practices and Materials* Plenum Press, New York 1988 and in Hepher, 1964, *The Journal of Photographic Sciences* 12:181–90, each of which is incorporated herein by reference in its entirety and for all purposes. Other materials are available from suppliers such as Olin Microelectonic Materials (Santa Clara, Calif.) and OCG Microelectronic Materials, Inc. (West Patterson, N.J.). Materials useful for positive photoresists, refered to herein as photodepolymerizable coatings, include quinone diazides, novalak resins, and acrylics. As described above, when an area of a photodepolymerizable coating is exposed to light, the material in that area is rendered more soluble than unexposed areas in a developer (e.g., a basic aqueous solution). In a most preferred embodiment, novalak resins and an aqueous developer are used.

L) Kits

The invention also includes kits for carrying out the methods described herein. Typically a kit will contain instructions and one or more of the following in a container: slides, solidifiable materials or components thereof, a photoinitiator, a photoreactive cross-linking agent, a photodepolymerizable coating, PCR primers, PCR reagents, a light source and an adhesive tape.

EXAMPLES

MATERIALS AND METHODS

A) Materials

Maternal blood and fetal umbilical cord blood between 12–18 weeks gestation was obtained from termination clinics after obtaining informed consent. Glass microscope slides were from a laboratory supply company and were washed with ethanol and air dried before use. In some experiments, slides were coated with solutions of poly-L-lysine, agarose, alginate, or chondroitin sulfate and air dried prior to deposition of blood cells. The stage micrometer (#36121) was from Edmund Scientific Company (Barrington, N.J.). Astrazon Blue was obtained from Miles Industrial Chemicals Division. Deionized water was from Stephen's Scientific (Riverdale, N.J.). Monomers, polymers, and crosslinkers were obtained from Aldrich Chemical Co. (Milwaukee, Wis.) unless otherwise indicated. UV10, UV14, UV71 were obtained from Masterbond, Inc. (Hackensack, N.J.). Waterclear Surfboard Resin is a commercial product manufactured by TAP Plastics, Inc. (Dublin, Calif.). BASED was obtained from Pierce (Rockford, Ill.). DNAse I Type IV from Bovine Pancreas (2300 Units/mg) was obtained from Sigma Chemical Co. (St. Louis, Mo.).

The FITC-labeled probe specific for X chromosome was obtained from Vysis, Inc. (Downer's Grove, Ill.), and a Cy-3-labeled probe specific for Y-chromosome was obtained from Cytocell Ltd. (Oxfordshire, U.K.).

Microscopy was carried out using a Zeiss microscope (model GFL) equipped with 100 W mercury arc lamp manufactured by Advanced Radiation Corporation (Santa Clara, Calif.) or a customized Olympus BX60 microscope which was flily computer controlled and equipped with a motorized stage, dual filter wheels and a CCD camera. The helium cadmium laser was from OmniChrome (Chino, Calif.) and the Omnigene thermocycler (Model No. TR3 SM5) was from Hybald Limited.

B) Sample Preparation and Identification of nfRBCs

Blood wedge smears (maternal blood, fetal cord blood, or mixed maternal and male fetal cord blood) were prepared, usually with 2 µl of blood applied per slide. In some cases, maternal blood was enriched for fetal nfRBCs as in U.S. Pat. No. 5,432,054, and deposited on chamber slides by centrifugal force. The cells were fixed by immersion of slides in 80% ethanol for 5 min. followed by 5 min. in 50% ethanol.

Kleihouer-Betke extraction was carried out by immersing slides in two changes of a fresh solution of 50 mM citrate-phosphate buffer, pH 3.3 for 1 min., followed by immersion in 50 mM citrate-phosphate buffer, pH 5.5.

Astrazon Blue staining of nuclei was for 3 min. in 0.005% Astrazon Blue, pH 5.5, followed by 3× immersion in each of two changes of deionized water, blotting with bibulous paper, and air drying. Following Kleihouer-Betke extraction and Astrazon Blue staining of nuclei, nfRBCs could be identified by the presence of a blue nucleus and of hemoglobin absorbance (415 nm) in the same cell.

C) Application of Solidifiable Material

A drop containing 75–100 µl of a solidifiable formulation was applied to the slide. Application of a coverglass two-thirds as long as the slide (24×60 mm) facilitated the formation of a thin film. The coverglass was then removed by smoothly sliding it horizontally across the slide. The slide was returned to the microscope and the target cell was relocated.

D) Illumination Source

A 100 W mercury arc lamp was used as a source of illumination. Studies of activation spectra, exposure time, and aperture size, were performed using a dichroic filter monochromator (Zeiss Catalog No. 4677883) placed between the mercury arc lamp and the microscope condenser.

E) Removal of Unpolymerized Plastic

Slides were dipped in organic solvent, usually tolulene, to remove unpolymerized material and allowed to air dry. For some plastic formulations, this was followed by immersion in 2,2-dioxane. The total time in organic solvent was 2–4 min.

F) Removal of Plastic Plugs

The slide was visually and microscopically inspected to determine the condition of the plastic plug(s). The target cell was exposed by carefully applying pressure to the edge of the plastic plug until it was released from the slide. The plastic plug was transferred to a sterile tube for amplification of the genetic material, if it was present, by PCR. After removal of the plug, the underlying section of the slide was examined to determine if the target cell (stained with Astrazon Blue) remained on the slide. If the target cell remained on the slide, analysis by florescent in situ hybridization was carried out.

G) Amplification

Target cells that remained attached to plastic plugs were subjected to polymerase chain reaction (PCR). DNA present in target cells was amplified for a Y-specific signal using the nested primer technique (Lo et al., 1993, *Human Genetics* 90: 493–88), and, in addition, using a primer specific for the male (Y) chromosome. Controls included known male and known female (non-pregnant) genomic DNA isolates plus a negative reaction control (no addition) and a positive control (male genomic DNA).

H) Florescent In Situ Hybridization (FISH)

FISH was carried out using standard techniques. Briefly, slides were treated with 80% acetic acid in deionized water for 5 min, to extract the cytoplasm, immersed in a phosphate based buffer containing detergent, washed (2×5 min.) in PBS, and dehydrated in 70%, 85%, and 100% ethanol (2 min. each). An aliquot of X- and Y-chromosome specific probes labeled, respectively, with FITC and Cy-3 were applied to a coverglass. The coverslip was applied to the slide by gently lowering the area of the slide for FISH over the drop of probe and allowing capillary action to draw the coverslip onto the slide. An Omnigene thermocycler was then used to denature the strands of DNA at 70° C., and to hybridize the probe to the single stranded DNA. After treating the slide in a series of formamide and buffer washes, the nuclei were counterstained with DAPI. Cells were then visualized by fluorescence microscopy. In situ hybridization (e.g., FISH) techniques are well known and are described generally in, e.g., Angerer et al., *Methods Enzymot.*, 152:649–660 (1987).

Example 1

DEVELOPMENT OF A LIGHT-ACTIVATED PROTECTIVE LAYER TO STABILIZE SINGLE CELLS OF INTEREST

This experiment demonstrates formulation of solidifiable compositions which become solid after exposure to light. Each of the formulations listed in Table 1 polymerized upon exposure to multichromatic light.

TABLE 1

PARTIAL LIST OF FORMULATIONS SUCCESSFULLY PHOTOPOLYMERIZED USING MULTICHROMATIC LIGHT FROM A MERCURY ARC LAMP.

| Formulation | Component 1 | Component II | Photoinitiator or Crosslinker | Ratio |
| --- | --- | --- | --- | --- |
| 1 | Neopentyl glycol dimethracrylate | Poly Bis Phenol A-co-epichlorohydrin | 2,2-dimethoxy,2-phenylacetophenone | 4.5:4.5:1 (wt:wt:wt) |
| 2 | Neopentyl glycol dimethacrylate | 5 minute epoxy | 2,2-dimethoxy,2-phenylacetophenone | 4.5:4.5:1 (wt:wt:wt) |
| 3 | Neopentyl glycol dimethacrylate | Waterclear Surfboard Resin | 2,2-dimethoxy,2-phenylacetophenone | 4.5:4.5:1 (wt:wt:wt) |

TABLE 1-continued

PARTIAL LIST OF FORMULATIONS SUCCESSFULLY PHOTOPOLYMERIZED USING MULTICHROMATIC LIGHT FROM A MERCURY ARC LAMP.

| Formulation | Component 1 | Component II | Photoinitiator or Crosslinker | Ratio |
|---|---|---|---|---|
| 4 | Waterclear Surfboard Resin[1,2] | | 2,2-dimethoxy,2-phenylacetophenone | 9:1 (wt:wt) |
| 5 | Waterclear Surfboard Resin | Styrene monomer | 2,2-dimethoxy,2-phenylacetophenone | 3:6:1 (wt:wt:wt) |
| 6 | UV71DC[3] | | | |
| 7 | UV14[2] | | | |
| 8 | UV10[2] | | | |
| 9 | Waterclear Surfboard Resin[1] | Poly Bis Phenol A-co-epichlorohydrin | BASED (20% wt/v in DMSO) | 1:1:1 (wt:wt:v) |
| 10 | Polybutylmethacrylate | trimethylol trimethacrylate | 2,2-dimethoxy,2-phenylacetophenone | 1:10:1 (wt:v:wt) |

[1]Waterclear Surfboard Resin is contains styrene monomer (approximately 40%) and polyester.
[2]Acetophenone was not an effective photoinitiator in an experiment with this formulation or with this formulation plus neopentyl glycol.
[3]UV71, UV14, and UV10 are commercially available products obtained from Master Bond, Inc (Hackensack, NJ). UV10 contains Bis-Phenol A type epoxy acrylate oligomer, polyethylene glycol dimethacrylate, silicon surfactant, and 2,2-dimethoxy,2-phenylacetophenone making it substantially similar to Formulation 1. UV14 contains penta-erythritol tetracrylate, urethane acrylate oligomer, 2,2-dimethy,2-phenylacetophenone, polyethylene glycol dimethacrylate, and methylphenylglyoxylate. UV71DC is a one-component, optically clear product containing polydimethylsiloxznes.

Example 2

EFFECT OF WAVELENGTH ON POLYMERIZATION

This experiment investigated the effect of specific wavelengths of light on polymerization. Tests carried out using poly bis phenol A-co-epichlorohydrin and neopentyl glycol dimethacrylate (Formulation 1) demonstrated that photopolymerization with this formulation requires the use of multichromatic light. Photopolymerization was performed on slides with a monolayer of maternal blood. A narrow wave band (bandwidth of approximately 10 nm) of activating light was varied. Exposures of 5, 10, 20, and 40 seconds were taken at each wavelength, and the resulting plastic plug size was recorded. No significant photopolymerization resulted from exposure to essentially monochromatic light (10 nm bandwidth) between 400–700 nm. Similarly, illumination using a helium-cadmium laser (442 nm) did not result in polymerization. However, full visible spectrum illumination with high pressure mercury arc resulted in formation of solid within 30 seconds.

Using wider band filters it was determined that deep blue light was effective, but green was ineffective for photopolymerization. The size of the photopolymerized plastic plug was significantly smaller when a defined range of the spectrum was blocked out with a filter than it was when full spectrum UV light was used for the same exposure time.

Example 3

EFFECT OF EXPOSURE TIME ON PLUG SIZE

Experiments were carried out to determine the effect of exposure time on the size of the plastic plug formed. Several formulations were tested using 2,2-dimethoxy-2-phenylacetophenone (10% w/v) as the photoinitiator, as shown in Table 1. Typically a 15–60 sec. exposure generated a photopolymerized plastic plug whose characteristics and underlying cells can be easily visualized microscopically within the field of view of a 10× objective. Photopolymerization with most of these formulations required as little as 5 sec. exposure to multichromatic light. It was observed that if the exposure time was doubled or a higher multiple of the minimum effective time was used, the size of the plug increased, although the relationship was not linear.

Example 4

CHOICE OF PHOTOINITIATOR

In this experiment, the effectiveness of three different acetophenones was evaluated. Photoinitiators 2,2-dimethoxy-2-phenyl acetophenone, 2,2-diethoxyacetophenone, or acetophenone were used to photopolymerize Waterclear Surfboard Resin, a commercial product containing polyester plus 40% styrene monomer. Using a ratio of 9:1 resin photoinitiator (by weight), exposure times of 1–5 min were tested. Formulations of 2,2-dimethoxy-2-phenyl acetophenone and 2,2-diethoxyacetophenone resulted in formation of a solid plug in 2 min. or less. Acetophenone was not effective in catalyzing the photopolymerization of styrene monomer. 2,2-dimethoxy-2-phenyl acetophenone was also most effective (i.e, fastest) in photopolymerizing a different formulation consisting of Surfboard Resin and Neopentyl glycol dimethacrylate. For all subsequent studies (i.e., the examples described infra), 2,2-dimethoxy-2-phenylacetophenone was used as the photoinitiator.

Example 5

USE OF APERTURES TO VARY PLUG SIZE

This example demonstrates that by using apertures of different sizes to fit in front of a mercury arc lamp, plastic plugs of various sizes can be created. An aperture system was implemented using a common metal washer with the same outside dimension as the commercial filter set for the mercury light housing. Aluminum foil was attached to the washer to close its central space, and pinholes of known size were drilled in the foil using miniature drillbits designed for fine work with a Dremmel tool. These apertures were placed in the light path close to the iris diaphragm that controlled the field aperture and were put into sharp focus by refocusing the substage condenser of the microscope. The diameter of the resulting illuminated area was then determined (Table 2). Using an aperture made with the #73 drillbit (approx. 0.6 mm diameter), a 5.21μ diameter area was illuminated. Using this aperture, it was repeatedly possible to photopolymerize a plastic spot equivalent to the diameter of 1 red blood cell. This demonstrates that a single fetal nfRBCs in a field of maternal cells can be protected.

TABLE 2

THE DIAMETER OF THE PHOTOPOLYMERIZED PLASTIC PLUG CAN BE CONTROLLED BY VARYING THE DIAMETER OF AN APERTURE.

| Drill Bit Number | Projected* Aperture Size (mm) | Calculated Diameter of the Aperture (μ) |
|---|---|---|
| 76 | 2.5–3 | 3.2 |
| 68 | 3.5 | 4.5 |
| 73 | 4 | 5.2 |
| 59 | 18 | 23.4 |
| 61 | 20 | 26.4 |

*The Edmund stage micrometer (Edmund Scientific) used has 100 rulings per mm. It was put on the Zeiss microscope and the image was projected onto a TV monitor. The monitor irnage was calibrated and it was determined that a 1 mm image on the monitor equaled 1.3μ on the slide.

Example 6

DESTRUCTION OF UNPROTECTED DNA

This example describes use of two methods for elimination undesired DNA from a slide while maintaining the protected DNA.

A) Acid Hydrolysis of DNA

Slides containing a monolayer of Astrazon Blue-stained adult blood were pretreated with 1 N HCl at room temperature, and treated with 1 N HCl at 60° C. for varying time periods up to 60 min. Ethidium bromide was used to detect DNA that remained after treatment with HCl. With increasing time of treatment, both the intensity of the ethidium bromide staining decreased and the number of stained cells per field of view decreased until, after 30 min. of treatment, no ethidium bromide stained cells were visible in any of 5 fields of view examined. The results of this experiment demonstrated that DNA could be fully destroyed by exposure to acid.

B) DNAse

Fetal cord blood deposited as wedge smears was fixed and stained with either Astrazon Blue or ethidium bromide. Plastic plugs made using Waterclear Surfboard Resin were photopolymerized over nfRBCs of interest. Slides containing one or more nfRBCs protected by photopolymerized plastic plugs were incubated at 37° C. with a solution of bovine pancreas DNAse I(11.5 units/ml in PBS containing 6% BSA and 10 mM magnesium acetate). Following DNAse treatment for 0, 10, or 30 min., the enzyme was removed by immersion three times in each of two changes of PBS and the slides were air dried and restrained with Astrazon Blue. All three slide had Astrazon Blue positive cells under the plastic plugs. In addition, numerous Astrazon Blue stained cells were present throughout the untreated (i.e., 0 min.) slide (i.e., in unprotected areas). The two treated slides (i.e., 10 and 30 min. treatment) were scanned over 168 fields at 200× magnification using an automated microscopy system and search parameters for identifying nfRBCs followed by visual examination. Between 60–80 objects were identified as possible nuclei on each slide by the automated system, primarily due to residual dye not associated with cells. Upon visual examination, only 1 stained cell was identified on each of the slides. In contrast, an untreated (i.e., 0 min.) control slide had approximately 15–20 visually confirmed nucleated cells per field.

Example 7

PRESENCE OF DNA IN PROTECTED CELLS

The presence of amplifiable DNA in single cells protected by the presence of the polymerized plug is demonstrated in this example.

Maternal blood was spiked with an aliquot of cord blood from a male fetus and deposited on two slides which were then fixed and stained with Astrazon Blue. The slides were scanned and fetal nfRBCs were identified and their precise location on the slide noted. Plastic (Formulation 10) was photopolymerized over the cells of interest using a 30 sec. exposure. Unpolymerized plastic was removed by tolulene extraction. One slide was treated with DNAse as described in Example 6. The plastic plugs were mechanically removed from each slide, and the presence of the underlying Astrazon Blue stained target cell was confirmed microscopically.

In the slide not treated with DNAse, eight nfRBCs were located. FISH was performed using a FITC-labeled probe specific for the X chromosome and a Cy-3-labeled probe specific for the Y chromosome. Of the eight target nfRBCs on this slide, seven were successfully identified as male by the presence of green and red signal over a DAPI stained nucleus located precisely in the location of the photopolymerization. This slide was not treated with DNAse, so as expected, it also contained maternal cells which were stained with dual signals corresponding to two FITC labeled X-chromosomes over a DAPI stained nucleus.

In the second slide, which was treated with DNAse immediately before removing the plastic plug, contained a green FITC signal plus a red Cy-3 signal over a DAPI stained nucleus corresponding to a male nfRBC containing XY chromosomes. However, there were no remaining DAPI nuclei stained with dual FITC (XX) signal on the slide, indicating that the cells not protected by plastic plugs (i.e., nucleated cells of maternal origin) were destroyed by the DNAse treatment.

Example 8

AMPLIFICATION OF DNA

Figure 4:
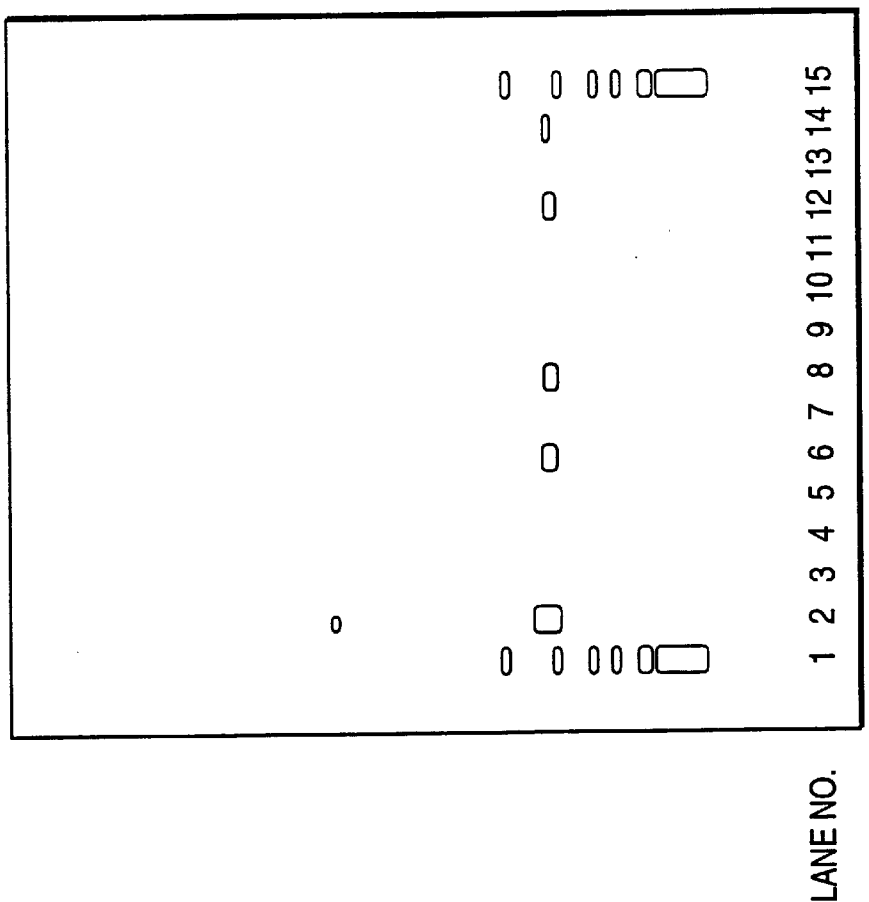
FIG. 4 shows the results of PCR amplification from a single protected nucleated fetal red blood cell. Lanes 1 and 15 are molecular weight standards, lanes 3, 5, 10 7, 9, 11, and 13 are blank, lane 2 is a positive control, and lane 4 is a negative control. Lanes 6, 8, 10, 12, and 14 correspond to amplification products from five different plugs.

This example shows the amplification of DNA present from single nfRBCs attached to plastic plugs using PCR technology. Five plugs with single nfRBCs from DNAse-treated slides were prepared as described in Example 7. The solid plugs were transferred to reaction tubes and PCR was carried out using primers specific for the DYS14 sequence of the human Y chromosome (Lo et al., 1993, *Human Genetics* 90:483–88). Of the five plugs, four produced amplification fragments of the expected size (FIG. 4). Thus, it was possible to identify, protect, and amplify DNA from rare male nfRBCs in a population of maternal cells.

For the purposes of clarity and understanding, the invention has been described in these examples and the above disclosure in some detail. It will be apparent, however, that certain changes and modifications may be practiced within the scope of the appended claims. All publications and patent applications are hereby incorporated by reference in their entirety for all purposes to the same extent as if each were so individually denoted.

What is claimed is:

1. A method for separating a rare cell from other cells in a cell population comprising:
    (a) applying cells from the cell population to a solid support;
    (b) determining the location of the rare cell on the solid support and overlaying the cells with a solidifiable material, wherein a cover layer is formed;
    (c) illuminating the cover layer with light focused at the location identified in step (b) whereupon a solid plug is formed from the solidifiable material at the location; and
    (d) removing the solid plug from the solid support, wherein the rare cell adheres to the solid plug,
    whereupon the rare cell is separated from other cells in the cell population.

2. A method for analyzing DNA of a rare cell in a cell population comprising:
    (a) applying cells from the cell population to a solid support;
    (b) determining the location of the rare cell on the solid support and overlaying the cells with a solidifiable material, wherein a cover layer is formed;
    (c) illuminating the cover layer with light focused at the location identified in step (b) whereupon a solid plug is formed from the solidifiable material at the location;
    (d) removing the solid plug from the solid support, wherein the rare cell adheres to the solid plug; and,
    (e) analyzing the DNA of the rare cell.

3. The method of claim 1 wherein the solidifiable material comprises at least one compound selected from the group consisting of ethylene, styrene, substituted stryenes, propylene, vinyl, vinyl alcohols, vinyl acetals, methacrylate, urethane, neopentyl glycol dimethracrylate, poly bis phenol A-co-epichlorohydrin, epoxy resin, bis-phenol A type epoxy acrylate oligomer, polyethylene glycol dimethacrylate, penta-erythritol tetracrylate, urethane acrylate oligomer, neopentyl glycol dimethracrylate, polyethylene glycol dimethracrylate, methylphenylglyoxylate, polybutylmethacrylate, and trimethylol trimethacrylate.

4. The method of claim 1 wherein the solidifiable material comprises 2,2-dimethoxy-2-phenyl acetophenone or 2,2-diethoxyacetophenone.

5. A method for analyzing DNA of a rare cell in a cell population comprising:
    (a) applying cells from the cell population to a solid support;
    (b) determining the location of the rare cell on the solid support, and overlaying the cells with a solidifiable material, wherein a cover layer is formed,
    (c) illuminating the cover layer with light focused at the location identified in step (b), whereupon a solid plug is formed from the solidifiable material at the location;
    (d) removing the solidifiable material which is not solidified;
    (e) treating the solid support with a DNA-inactivating agent;
    (f) removing the solid plug from the solid support to expose the rare cell; and
    (g) analyzing the DNA of the rare cell.

6. The method of claim 5 wherein the rare cell is a fetal cell, and the cell population is maternal blood.

7. The method of claim 6 wherein the fetal cell is a nucleated red blood cell.

8. The method of claim 5 wherein the rare cell is a malignant cell.

9. The method of claim 3 wherein the cell population is in a tissue section.

10. The method of claim 5 wherein the solidifiable material comprises at least one compound selected from the group consisting of ethylene, styrene, substituted stryenes, propylene, vinyl, vinyl alcohols, vinyl acetals, methacrylate, urethane, neopentyl glycol dimethracrylate, poly bis phenol A-co-epichlorohydrin, epoxy resin, bis-phenol A type epoxy acrylate oligomer, polyethylene glycol dimethacrylate, penta-erythritol tetracrylate, urethane acrylate oligomer, neopentyl glycol dimethracrylate, polyethylene glycol dimethracrylate, methylphenylglyoxylate, polybutylmethacrylate, and trimethylol trimethacrylate.

11. The method of claim 5 wherein the solidifiable material comprises 2,2-dimethoxy-2-phenyl acetophenone or 2,2-diethoxyacetophenone.

12. The method of claim 11 wherein the solidifiable material comprises 2,2-dimethoxy-2-phenyl acetophenone.

13. The method of claim 5 wherein the analysis is carried out after the rare cell is removed from the solid support.

14. The method of claim 5 wherein the analysis of the DNA from the rare cell comprises amplifying the DNA of the rare cell.

15. The method of claim 14 wherein the amplification is by the polymerase chain reaction.

16. The method of claim 14 wherein the amplification is by the ligase chain reaction.

17. The method of claim 14 wherein the amplification is carried out after the rare cell is removed from the solid support.

18. A kit comprising a container comprising slides and at least one of a photoreactive cross-linker, a photoinitiator, and a plastic monomer.

19. A method for amplifying DNA of a rare cell in a cell population comprising:
    (a) applying cells from the cell population to a solid support;
    (b) determining the location of the rare cell on the solid support, and overlaying the cells with a photodepolymerizable coating, wherein a cover layer is formed;
    (c) heating the cover layer to make it solid;
    (d) illuminating the cover layer with light focused at the location identified in step (b) to solubilize the cover layer at the location, whereby solubilized material is produced at the location;
    (e) removing the solubilized material; whereupon the rare cell is exposed; and,
    (f) amplifying the DNA of the rare cell.

20. The method of claim 18, wherein the photodepolymerizable coating is a novalak resin.

* * * * *

UNITED STATES PATENT AND TRADEMARK OFFICE
CERTIFICATE OF CORRECTION

PATENT NO. : 6,087,134
DATED : July 11, 2000
INVENTOR(S) : Alexander Michael Saunders It is certified that error appears in the above-identified patent and that said Letters Patent is hereby corrected as shown below:

Column 20, line 58, replace "18" with --19--.

Signed and Sealed this

Tenth Day of April, 2001

Attest:

NICHOLAS P. GODICI

*Attesting Officer*    *Acting Director of the United States Patent and Trademark Office*